US00PP26293P3

(12) United States Plant Patent
Schoone

(10) Patent No.: US PP26,293 P3
(45) Date of Patent: Jan. 5, 2016

(54) ***PHALAENOPSIS* ORCHID PLANT NAMED 'PIXIE'**

(50) Latin Name: *Phalaenopsis hybrida*
Varietal Denomination: Pixie

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 140 days.

(21) Appl. No.: 13/998,019

(22) Filed: Sep. 24, 2013

(65) Prior Publication Data

US 2014/0090134 P1 Mar. 27, 2014

Related U.S. Application Data

(60) Provisional application No. 61/705,239, filed on Sep. 25, 2012.

(30) Foreign Application Priority Data

Sep. 27, 2012 (NL) ..... PBR OPS963

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — Foley & Lardner LLP; Sunit Talapatra

(57) ABSTRACT

A new and distinct *Phalaenopsis* plant named 'Pixie' particularly characterized by flowers which are purple with white edges and a purple labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Pixie'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Pixie'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Pixie' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Pixie' originated from a cross made by the inventor in 2000 in Strengweg, Heemskerk, The Netherlands. The female or seed parent is the *Phalaenopsis* cultivar designated 'Carmela's Pixie', unpatented. The male or pollen parent is the *Phalaenopsis* cultivar designated 'King Shiang's Rose', unpatented. The new *Phalaenopsis* 'Pixie' was discovered and selected by the inventor as a single flowering plant within the progeny of the stated cross in a controlled environment in 2008 in Strengweg, Heemskerk, The Netherlands.

Asexual reproduction of the new *Phalaenopsis* cultivar by tissue culture was first performed in July, 2008 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Pixie', which in combination distinguish this *Phalaenopsis* as a new and distinct cultivar:

1. flowers which are purple with white edges and a purple labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Pixie', the female parent 'Carmela's Pixie' has white with purple flowers and are about 5 to 6 cm in size. The male parent 'King Shiang's Rose' has pink/red colored flowers and are about 4 to 5 cm in size, whereas the flowers of 'Pixie' are purple with white edges and are about 4 cm in size.

Presently, the commercial cultivar to which 'Pixie' can be meaningfully compared is 'Spoiled Brat' (unpatented). They both have a large labellum, only the labellum of 'Pixie' is purple and the labellum of 'Spoiled Brat' is more red/purple. 'Pixie' has much more white on the petals and sepals than 'Spoiled Brat' and the flowers of 'Spoiled Brat' are larger than the flowers of 'Pixie'.

BRIEF DESCRIPTION OF THE PHOTOGRAPHS

The accompanying photographs illustrate the overall appearance of the new *Phalaenopsis* 'Pixie' showing the colors as true as is reasonably possible with colored reproductions of this type. Colors in the photographs may differ slightly from the color values cited in the detailed botanical description, which accurately describe the color of 'Pixie'.

DETAILED BOTANICAL DESCRIPTION

Figure 1:
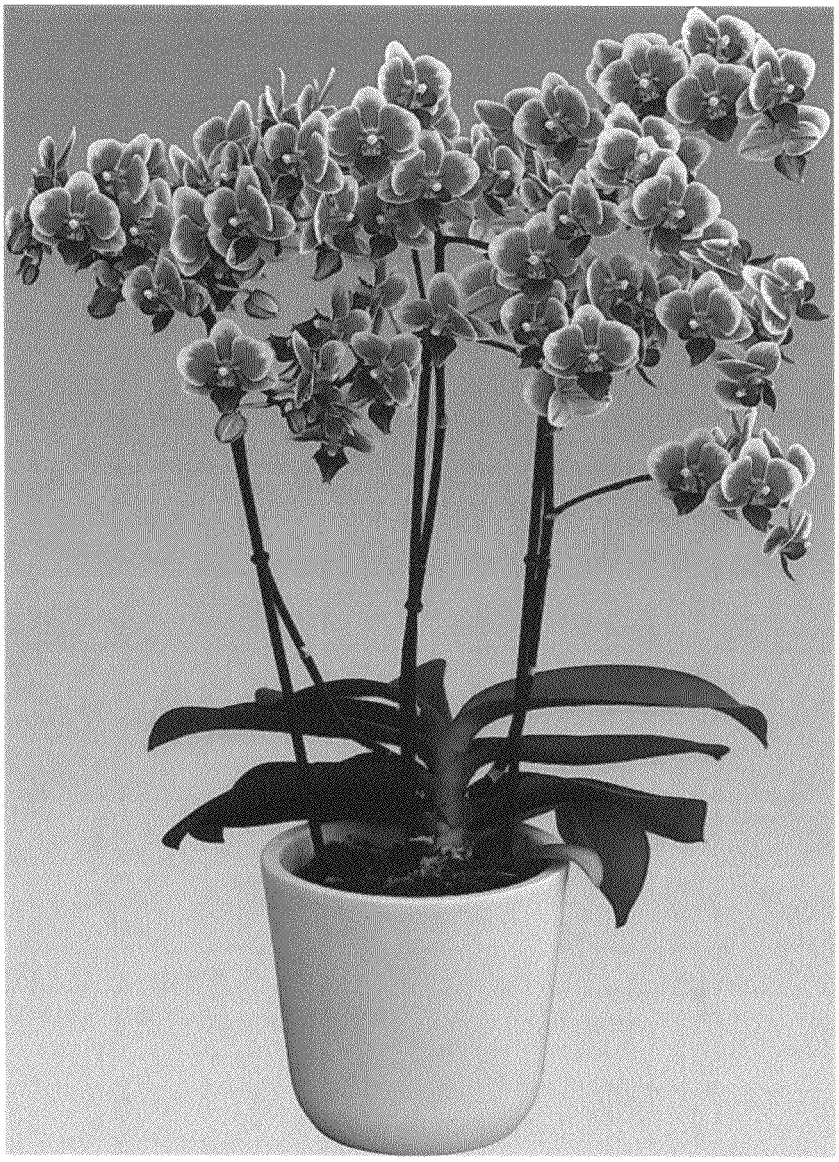
FIG. 1 shows a side view perspective of a typical flowering plant of 'Pixie' in a 12 cm pot, at 16 months of age.

The new *Phalaenopsis* cultivar 'Pixie' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Pixie' as grown in a greenhouse in Strengweg, Heemskerk, The Netherlands, under conditions which closely approximate those generally used in commercial practice. Initially, the ideal temperature to grow plants of 'Pixie' is 27° C. during the day and at night. Then, during the flowering phase of 'Pixie', the ideal growing temperature is 20-22° C. during the day and 18° C. at night. Light levels for growing 'Pixie' are a minimum of 5,000 lux and a maximum of 10,000 lux. A balanced fertilizer with level of 200 ppm N, 87 ppm P, 168 ppm K is applied. Duration of growth of 'Pixie' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Pixie' plants described is 12 months after potting.

Classification:

*Botanical.—Phalaenopsis hybrida.*

Parentage:

*Female or seed parent.—Phalaenopsis* cultivar designated 'Carmela's Pixie', unpatented.

*Male or pollen parent.—Phalaenopsis* cultivar designated 'King Shiang's Rose', unpatented.

Propagation:

*Type.*—Tissue culture.

*Rooting habit and description.*—Fleshy; approximately 4 mm-7 mm wide and grey/green in color (RHS 193B); freely branching. It takes 12 weeks for plants growing in tissue culture to initiate roots.

Plant:

*Size at maturity.*—Height (from bottom of pot to highest flower): about 50 cm. Spread: about 50 cm.

*Growth habit.*—Small; green leaves (RHS 141B) and a relatively large raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-3 racemes with flowers appear.

Foliage:

*Quantity per plant.*—About 6 to 9 leaves are produced before flowering.

*Arrangement and attachment.*—Half up/horizontal and on two sides.

*Overall shape of leaf.*—Oval, the tip is blunt and asymmetric.

*Texture (upper & underside).*—Smooth and leathery.

*Pubescence.*—None.

*Mature leaf length.*—About 12 to 16 cm.

*Mature leaf width.*—About 6 to 8 cm.

*Mature leaf thickness.*—About 2 mm.

*Mature leaf color (upper surface).*—Green (RHS 141B).

*Mature leaf color (under surface).*—Green (RHS 143C).

*Leaf base.*—Acute.

*Margin.*—Entire.

*Venation.*—Pattern: parallel. Color of midvein: upper surface: green (RHS 141B). Under surface: green (RHS 143C).

Inflorescence description:

*Appearance.*—Upright to slightly pendant, racemose inflorescence with bilaterally symmetrical flowers that open in succession beginning with the lowermost flower.

*Raceme.*—Quantity per plant: about 1 to 3. Number of flowers per raceme: about 35. Length: about 42 cm.

*Peduncle.*—Diameter: about 3 to 5 mm. Strength: strong. Aspect: upright. Texture: glabrous and smooth. Color: brown (RHS 200B) with green spots (RHS 143C).

*Buds.*—Height (from base to tip): about 15 mm. Diameter (at midpoint): about 11 mm. Shape: oval with a rounding on the side. Color: yellow/green (RHS 147D) with some red/purple (RHS 71A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 1-3 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
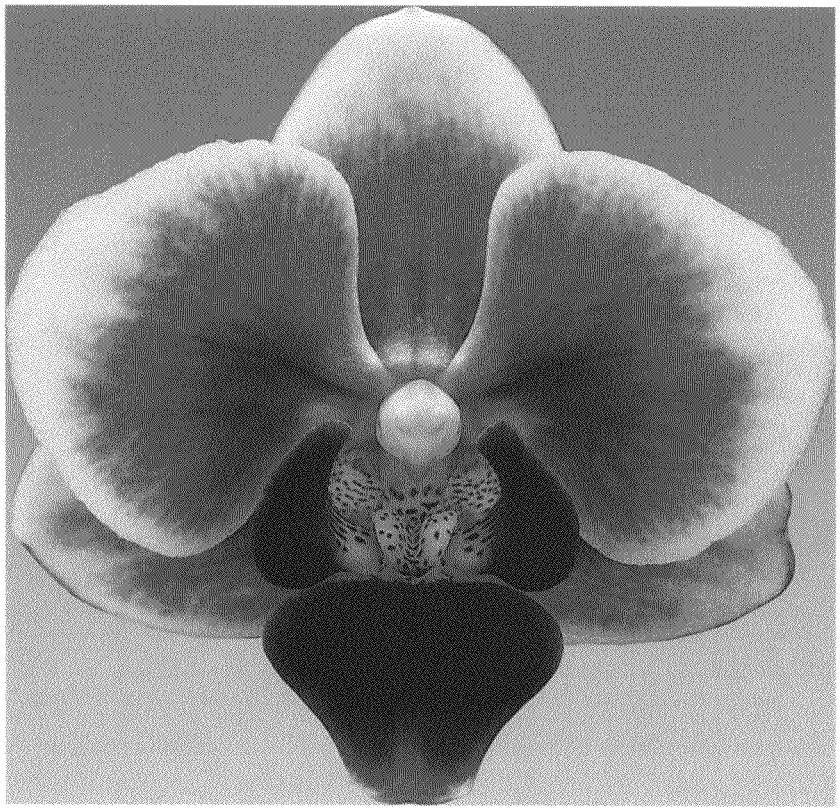
FIG. 2 shows a close-up view of a typical flower of 'Pixie'.
Figure 3:
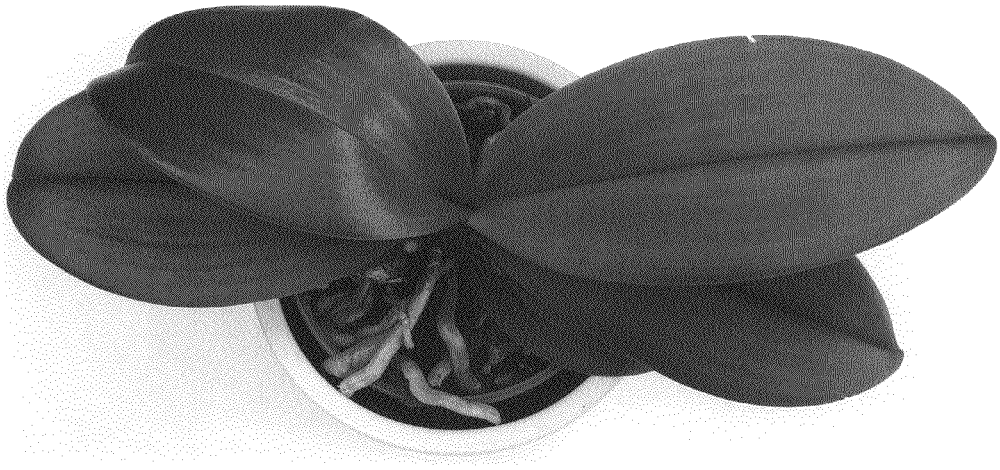
FIG. 3 shows a close-up view of the typical leaves of 'Pixie'.

*Flower*.—Rate of opening: Flowers fully opened about 2 to 3 days after petal and sepal separation. Orientation at opening: slanted upward and outward. Shape: Typical shape of *Phalaenopsis* orchid; see FIG. 2. Size (of single bloom): Height: about 3 cm. Diameter: about 4 cm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and a labellum. 2 lateral petals: Overall shape: broadly ovate and weakly cupped. Apex: round. Margin: entire and weakly undulate. Base: broadly ovate. Length: about 21 mm. Width: about 18 mm. Texture: Upper surface: smooth and satiny. Under surface: smooth and satiny. Color (when fully opened) upper surface: purple (RHS N78A). At the base and all around the edges white (RHS NN155D). Under surface: purple (RHS N78C). At the base and all around the edges white (RHS NN155D). Labellum: Overall shape: 3-lobed with 2 prominent callosities at central junction of the lateral lobes and base of the midlobe. Lateral lobes of labellum fold upward about the column; the midlobe extends forward and is terminated by 2 stubs appendages at the apex. Lateral lobes of the labellum are ovate in shape while the midlobe is triangular with a bump and a rib on it. Margin: entire and weakly undulate. Apex: oval. Length: about 15 mm. Width (not flattened): about 15 mm. Depth of tube created by lateral lobes of labellum: about 10 mm. Texture: Upper & under surface: smooth and satiny. Color (when fully opened): Midlobe: upper surface: At the base, in the center red/purple (RHS 59A). the rest is purple (RHS N78A). At the bottom on the edges some white (RHS NN155D). At the base also thin edges of yellow/orange (RHS 15A). Under surface: In the center from top till bottom white (RHS N155D). From base till the corners, the edges are grey/red (RHS 179A) which runs into purple (RHS N78A) and then into RHS N78D. Lateral lobes: upper surface: At the base white (RHS NN155D) with some red/purple stripes/spots (RHS 59A). Upper half is purple (RHS N78A). Lower edge is red/purple (RHS 59A). Under surface: At the base white (RHS NN155D) which runs into RHS 76C and then into purple (RHS N78A). Cirrhi: small (about 2 mm). Color: white (RHS NN155D). Pestle (Callosities): Length: about 3 mm. Width (not flattened): about 4 mm. Color: yellow (RHS 7A) with white (RHS NN155C) and with red/purple spots (RHS 59B).

*Sepals*.—Arrangement: Outer whorl comprises 3 sepals, one dorsal and two lateral sepals. Overall shape: egg-shaped. Length: about 18 mm. Width: about 14 mm. Margin: entire and weakly undulate. Apex: oval, little pointy. Texture: Upper & under surface: smooth and satiny. Color (when fully opened): Upper surface: Dorsal: purple (RHS N78A). At the base and all the edges are white (RHS NN155D). Lateral: purple (RHS N78A). At the base and all the edges are white (RHS NN155D). In the white at the base are also some red/purple spots (RHS 59B). Under surface: Dorsal & lateral: purple (RHS N78C) with on the edges white (RHS NN155D). On the midvein little darker purple (RHS N78A).

*Pedicel*.—Length: about 16 to 21 mm. Diameter: about 2 mm. Texture: glabrous and smooth. Color: purple (RHS N78D) and white (RHS N155B).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 9 mm. Diameter: about 4 mm. Color: white (RHS NN155D) and some purple (RHS N78B).

*Pollinia*.—Quantity: two. Size: about 1 mm. Color: yellow/orange (RHS 24A).

*Ovary*.—Length: about 2 mm. Diameter: about 1 mm. Color: white (RHS NN155D) with little purple (RHS N78A).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Pixie', as illustrated and described herein.

* * * * *